United States Patent
Kerner et al.

(10) Patent No.: US 7,436,498 B2
(45) Date of Patent: Oct. 14, 2008

(54) APPARATUS FOR DETERMINING THE SHAPE OF A GEMSTONE

(75) Inventors: Avi Kerner, Herzelia (IL); Yedidya Ariel, Dolev (IL); Nur Arad, Tel Aviv (IL)

(73) Assignee: Sarin Technologies Ltd., Ramat-Gan (IL)

( * ) Notice: Subject to any disclaimer, the term of this patent is extended or adjusted under 35 U.S.C. 154(b) by 32 days.

(21) Appl. No.: 11/448,916

(22) Filed: Jun. 8, 2006

(65) Prior Publication Data

US 2007/0285650 A1    Dec. 13, 2007

(30) Foreign Application Priority Data

Jun. 8, 2005    (IL) ..................................... 176196

(51) Int. Cl.
  G01N 21/00    (2006.01)
  G01B 11/24    (2006.01)
  G01B 11/30    (2006.01)
  G01B 11/245   (2006.01)

(52) U.S. Cl. .................. 356/30; 356/601; 356/603; 356/608; 356/613

(58) Field of Classification Search .................. 356/30, 356/601, 603, 608, 613
See application file for complete search history.

(56) References Cited

U.S. PATENT DOCUMENTS

| | | | |
|---|---|---|---|
| 3,610,756 A * | 10/1971 | Lenzen et al. ................. 356/30 |
| 3,947,120 A * | 3/1976 | Bar-Issac et al. .............. 356/30 |
| 4,302,097 A * | 11/1981 | Chlestil ........................ 355/52 |
| 4,417,564 A * | 11/1983 | Lawrence et al. ........ 125/30.01 |
| 4,529,305 A * | 7/1985 | Welford et al. ................ 356/30 |
| 5,076,698 A * | 12/1991 | Smith et al. .................. 356/602 |
| 6,567,156 B1 | 5/2003 | Kerner |
| 6,870,606 B2 * | 3/2005 | Klingler ....................... 356/30 |
| 7,259,839 B2 * | 8/2007 | Sivovolenko ................. 356/30 |
| 7,284,396 B2 * | 10/2007 | Barron et al. .................. 63/32 |
| 2001/0023925 A1 * | 9/2001 | Smith ......................... 250/372 |
| 2003/0019852 A1 * | 1/2003 | Kaplan et al. .......... 219/121.68 |

* cited by examiner

Primary Examiner—Gregory J. Toatley, Jr.
Assistant Examiner—Bryan J Giglio
(74) Attorney, Agent, or Firm—The Nath Law Group; Jerald L. Meyer; Derek Richmond

(57) ABSTRACT

An apparatus for determining the shape of a gemstone, including irregularities on its surface, is provided, The apparatus comprises a platform adapted to support the gemstone, a scanning system adapted to provide geometrical information concerning the three-dimensional convex envelope of the gemstone, an illumination system adapted to project on the gemstone a plurality of laser beams, an imaging system adapted to capture reflections of at least a part of said laser beams from the surface of the gemstone, and a processor. The processor is adapted to calculate, based on said geometrical information, a predicted reflection of each laser beam, to compare the captured reflections with said predicted reflections and to relate each captured reflection to its corresponding predicted reflection, to determine said shape of the gemstone based on the comparison and said geometrical information.

33 Claims, 10 Drawing Sheets

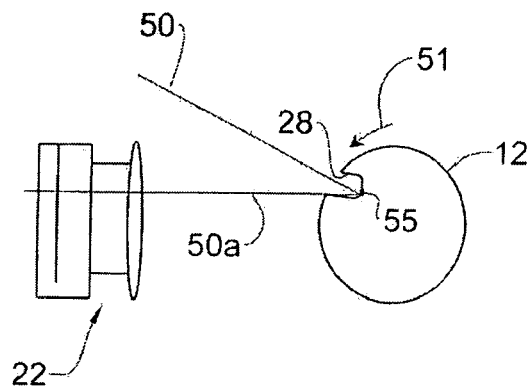
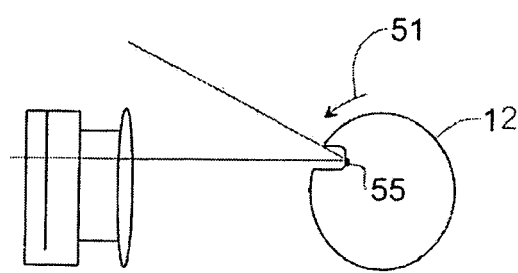
FIG. 11A                    FIG. 11B
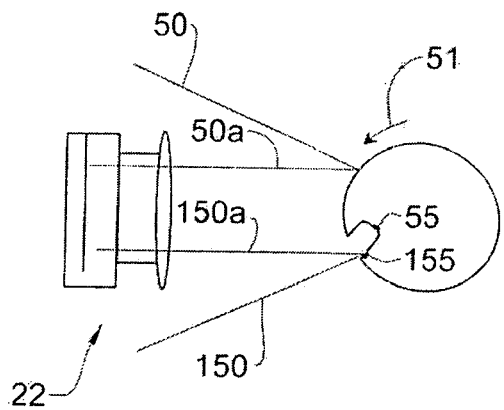
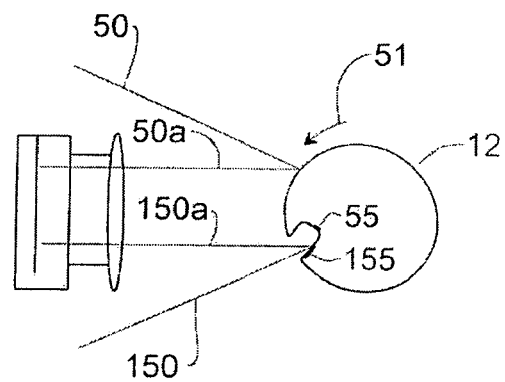
FIG. 11C                    FIG. 11D

APPARATUS FOR DETERMINING THE SHAPE OF A GEMSTONE

FIELD OF THE INVENTION

This invention relates to an apparatus for the inspection of a gemstone to determine the shape thereof.

BACKGROUND OF THE INVENTION

Finished gemstones which are available to a consumer are cut from a rough gemstone. In order to determine the optimal way to cut or saw the rough gemstone, it must first be inspected.

This inspection may be done by a trained professional, who then marks the rough gemstone with sawing line(s) to indicate to a stonecutter how to form one or more finished stones from the rough stone.

Alternatively, systems have been developed to automatically inspect and mark sawing lines on the rough stones. These systems typically first map the rough stone to determine its shape, then determine how to best cut it, and finally mark a sawing line thereon. One example of such a mapping and marking system is DiaMark™ produced by Sarin, Technologies Ltd, Ramat Gan, Israel.

In the latter type of system, a gemstone to be mapped is rotated, its three dimentional silhouette is determined, and its surface is imaged, at a plurality of angular positions of the stone, whereby the shape of the stone is determined including concavities on its surface.

One way of mapping a gemstone is described in the Applicant's U.S. Pat. No. 6,567,156, where in order to determine concavities on the surface of a gemstone, structured light triangulation is used, in which a laser beam is directed at the stone at various angular positions thereof, its reflection captured and compared to the reflection that would be received from a hypothetical gemstone having the same 3-D silhouette. Defects and concavities are indicated by deviations of the captured reflection from that which would be detected from the hypothetical gemstone.

SUMMARY OF THE INVENTION

According to one aspect of the present invention, there is provided an apparatus for determining the shape of a gemstone including irregularities (e.g., concavities and defects) on its surface, the apparatus comprising a platform adapted to support the gemstone, a scanning system adapted to provide geometrical information (such as Cartesian or polar coordinates) concerning the three-dimensional convex envelope of the gemstone, an illumination system adapted to project on the gemstone illumination in the form of at least two laser beams along two separate optical paths, an imaging system adapted to capture at least a portion of said illumination when reflected from the gemstone, and a processor adapted to determine said shape based on the captured illumination and the geometrical information, the apparatus being adapted to rotate the gemstone with respect to the illumination system about an axis of rotation, and at least one of said optical paths is spaced from the axis.

According to another aspect of the present invention, there is provided an apparatus for determining the shape of a gemstone including irregularities on its surface, the gemstone having a size being no greater than a predetermined maximal size, the apparatus comprising a platform adapted to support the gemstone, a scanning system adapted to provide geometrical information concerning the three-dimensional convex envelope of the gemstone, an illumination system adapted to project on the gemstone illumination in the form of a plurality of laser beams, an imaging system adapted to capture at least a portion of the illumination when reflected from the gemstone, and a processor adapted to determine said shape based on the captured illumination and said geometrical information, the plurality of laser beams comprises a first extreme laser beam a second extreme laser beam, and the remainder of the laser beams being therebetween, said extreme laser beams spaced from each other at least in the vicinity of the platform to a distance greater than said maximal size of the gemstone.

In the apparatus according to both above aspects of the invention, the processor may provide said shape in the form of a composite three-dimensional representation of the gemstone, which may be displayed or used in any manner known in the art.

The laser beams may be of a linear or any other appropriate shape.

The relative rotation of the gemstone with respect to the illumination system may be provided by the rotation of the platform or by the rotation of the illumination system and imaging system.

In accordance with one embodiment of the apparatus of this aspect of the invention, the illumination system may comprise a multi-beam laser source, and in accordance with another embodiment it may comprise at least two laser sources, each of which projects at least one laser beam. In both embodiments it is suggested that the optical paths of two adjacent laser beams form between them a predetermined angle, said angle and the distance between the illumination system and the platform supporting the gemstone being such as to ensure that the two optical paths of the laser beams pass through a gemstone of a predetermined minimal size, to be examined by the apparatus. This angle may be, for example, in the range between 0.05° and 10°.

The imaging system may comprise a camera having a detector such as a CCD.

The scanning system may comprise at least the imaging system and a light source facing the platform and being disposed substantially opposite the imaging system, to determine the silhouettes of the gemstone at a plurality of angular positions thereof, in which case the convex envelope may be a composite of the silhouettes of the gemstone calculated by the processor.

According to a further aspect of the present invention, there is provided an apparatus for determining the shape of a gemstone including irregularities on its surface, comprising a platform adapted to support the gemstone, a scanning system adapted to provide geometrical information concerning the three-dimensional convex envelope of the gemstone, an illumination system adapted to project on the gemstone a plurality of laser beams, an imaging system adapted to capture reflections of at least a part of said laser beams from the surface of the gemstone, and a processor adapted to calculate, based on said geometrical information, a predicted reflection of each laser beam, to compare the captured reflections with said predicted reflections and to relate each captured reflection to its corresponding predicted reflection, to determine said shape of the gemstone based on the comparison and said geometrical information.

According to this aspect, simultaneous scanning by multiple laser beams is facilitated. As such, only one rotation is required in order to achieve the scans from the different laser beams, thereby reducing the total time necessary for scanning.

By relating each captured reflection with its corresponding predicted reflection, the use of a plurality of laser beams projected at the same time is enabled.

According to one embodiment, the relating is accomplished by determining the proximity of each of the captured reflections to a predicted reflection.

According to another embodiment, the relating is accomplished by determining the side at which each captured reflection falls with respect to each predicted reflection.

According to a further embodiment, each laser beam is of a different wavelength, wherein the relating is accomplished based on the wavelength thereof.

According to a still further embodiment, each laser beam is projected at a different time. The relating is accomplished by establishing the laser beam which corresponds to the time at which each of the captured reflections is captured.

It will be appreciated that according to any of the above aspects, when multiple laser beams are projected from a single source, the gemstone may be rotated faster, thus reducing the time necessary to scan the surface of an entire gemstone. This is due to the fact that for each angular position of the gemstone, a larger area of the surface of the gemstone is scanned in comparison to scanning by a single laser beam. Therefore, scanning of the gemstone may take place at fewer angular positions thereof, without reducing the accuracy, at least when compared with scanning by a single laser beam from a laser beam source.

BRIEF DESCRIPTION OF THE DRAWINGS

In order to understand the invention and to see how it may be carried out in practice, embodiments will now be described, by way of non-limiting examples only, with reference to the accompanying drawings, in which:

FIGS. 10B through 10J (FIG. 10I intentionally omitted) are top views of the gemstone illustrated in FIG. 10A at different angular positions;

FIGS. 11A and 11B illustrate a gemstone, at different angular positions thereof, with a single laser beam impinging thereupon;

FIGS. 11C and 11D illustrate the gemstone seen in FIGS. 1A and 1B at other angular positions thereof, with an additional single laser beam from a second source impinging thereupon; and FIGS. 11E through 11J (FIG. 11I intentionally omitted) illustrate the gemstone shown in FIGS. 11A through 11D, with several laser beams from a single source impinging thereupon.

DETAILED DESCRIPTION OF EMBODIMENTS

Figure 1A:
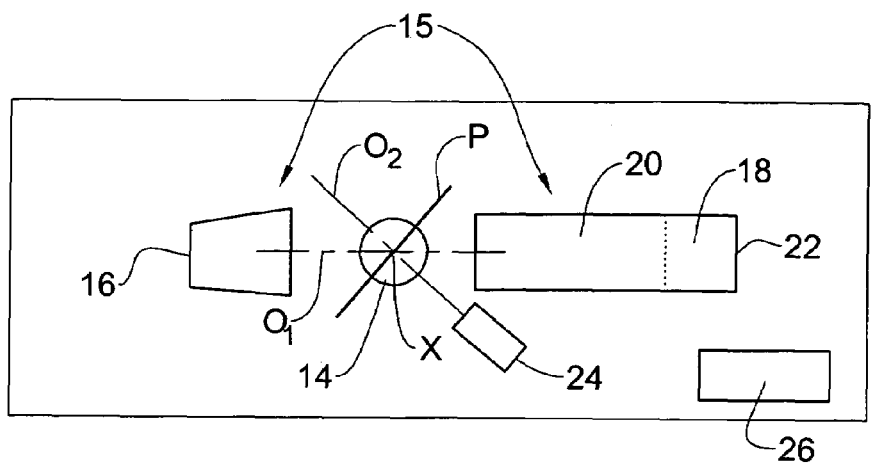
FIG. 1A is schematic illustration of one example of an apparatus according to the present invention.

As illustrated schematically in FIG. 1A, there is provided an apparatus, generally indicated at 10 comprising a gemstone supporting platform 14 (also referred to in the art as a "dop"), a processor 26, and a mapping device (not designated) including a scanning system 15 and a laser illumination system 24. The apparatus further comprises means (not shown) for the provision of relative rotation between the platform 14 and the mapping device around an axis of rotation X. This may be achieved either by the rotation of the platform 14 or by the rotation of the mapping device.

Figure 2A:
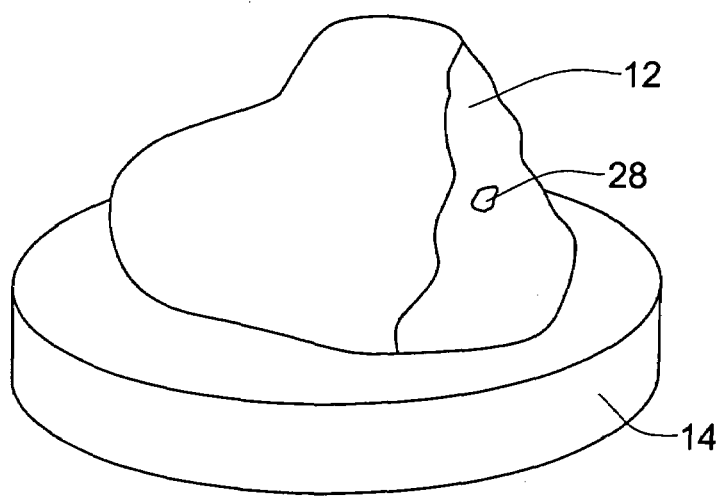
FIG. 2A is a schematic perspective view of a gemstone having a concave defect.

The apparatus 10 is designed to determine the shape of gemstones including irregularities on their surfaces, by mounting each such gemstone on the platform 14 and mapping it by the mapping device, the gemstones having their cross-sectional dimension at a predetermined height along the axis of rotation X, not less than a minimal dimension $D_{min}$ and not greater than a maximal dimension $D_{max}$. FIG. 2A shows such gemstone 12 having a concavity 28.

The scanning system 15 includes a backlight 16 and an imaging system 22 located on an optical axis $O_1$ crossing the axis of rotation X. It is adapted to determine the silhouettes of the gemstone 12 at a plurality of angular positions thereof. The outline of one such silhouette is indicated by line 32a in FIG. 2B, and as seen it does not include the concavity 28, indicated therein by dotted line 32b.

The imaging system 22 typically comprises a camera portion 18, which may be a CCD or other light-sensitive device, and an optics portion 20, which may comprises lenses (not indicated) adapted to project the light from the backlight 16 and the laser beams reflected from the gemstone to the camera portion. The optics 20 may be a telecentric lens arrangement, as known in the art. Using such an arrangement has the advantage that when diffuse light is reflected from the gemstone, only those rays which are parallel to the optical axis of the imaging system 22 reach the camera portion 18.

The illumination system 24 has an optical axis $O_2$ intersecting the axis $O_1$ at the axis of rotation X and defining with the optical axis $O_1$ an acute angle (not designated) such as to allow the imaging system to capture at least a portion of illumination projected by the illumination system 24 when reflected from the gemstone.

Figure 1B:
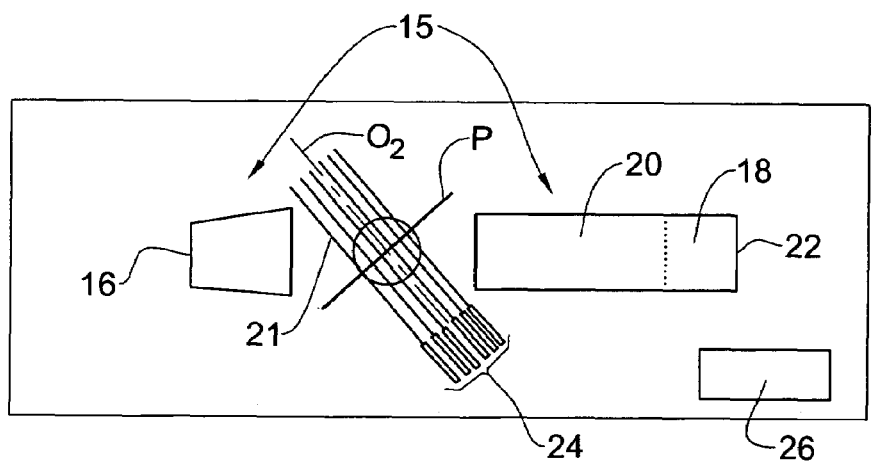
FIG. 1B is a schematic illustration of the apparatus illustrated in FIG. 1A, showing projected laser beams.
Figure 1C:
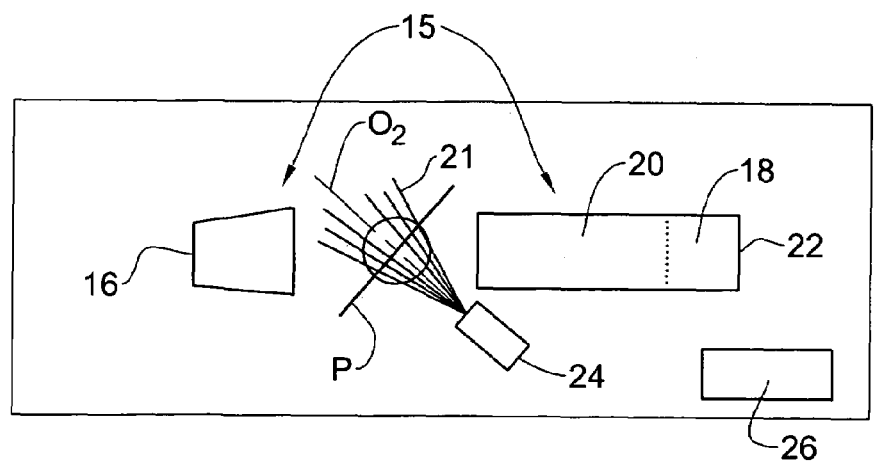
FIG. 1C is a schematic illustration of another example of the apparatus illustrated in FIG. 1A, showing projected laser beams.

The illumination system 24 is adapted to produce a plurality of laser beams 21 along their respective different optical paths all passing through a plane P which includes the axis of rotation X and is oriented perpendicularly to the optical axis $O_2$. The optical paths of the laser beams may be parallel to the optical axis $O_2$ or may form angles therewith. In the former case, the illumination system 24 may include an array of laser sources, such as shown in FIG. 1B, and in the latter case it may include a single multi-beam source, such as shown in FIG. 1C.

Figure 1D:
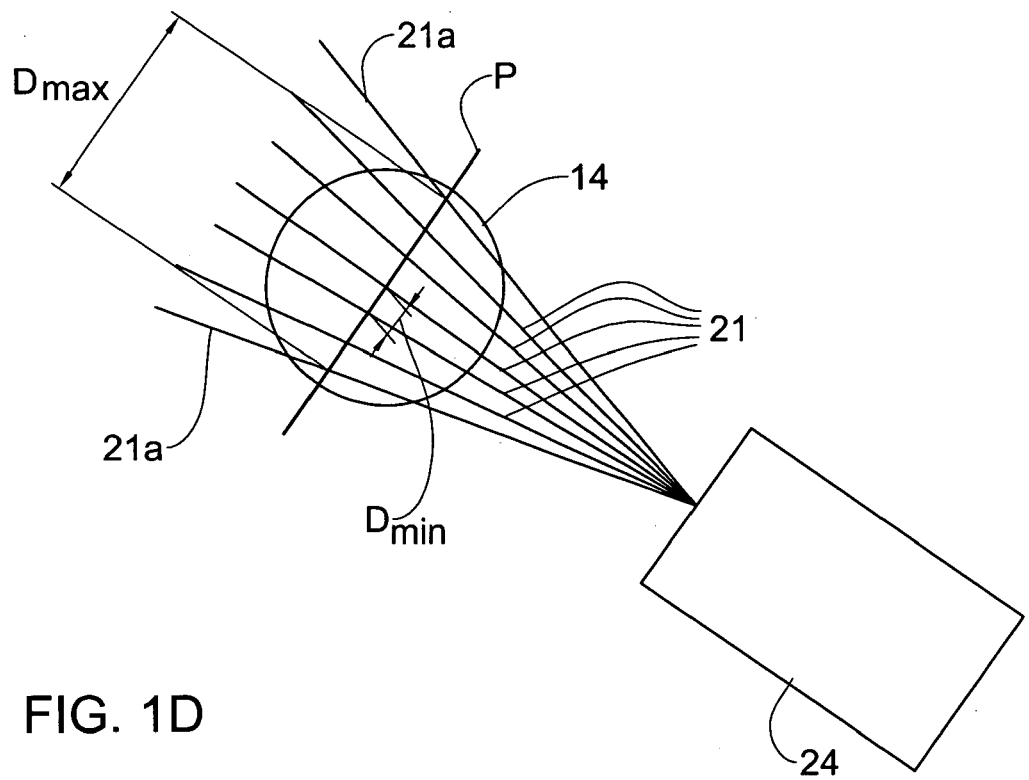
FIG. 1D is a closeup of an illumination system and platform of the apparatus illustrated in FIG. 1B.

As seen in FIG. 1D, the plurality of laser beams includes two extreme laser beams 21a whose optical paths intersect the plane P at locations spaced from each other by a distance greater than $D_{max}$. For example, this distance may be in the range between 10 mm and 40 mm. The plurality of laser beams is further characterized by a pitch between two adjacent laser beams being such that optical paths of two adjacent laser beams intersect the imaginary plane P at locations spaced from each other by distance smaller than $D_{min}$. For example, this distance may be in the range between 0.5 mm and 3 mm.

By providing the laser beams as described in connection with FIG. 1D, optimal imaging of the entire surface of the gemstone may be realized. The resolution of the final image of the gemstone depends on the pitch between adjacent laser beams, as will become clear below. By ensuring that the total spread of laser beams (defined as the spacing or pitch between extreme laser beams 21a) intersects plane P across a distance which is greater than the lo maximal dimension $D_{max}$ of the gemstone, the maximal amount of the surface of the gemstone is imaged at each angular position thereof.

Figure 1E:
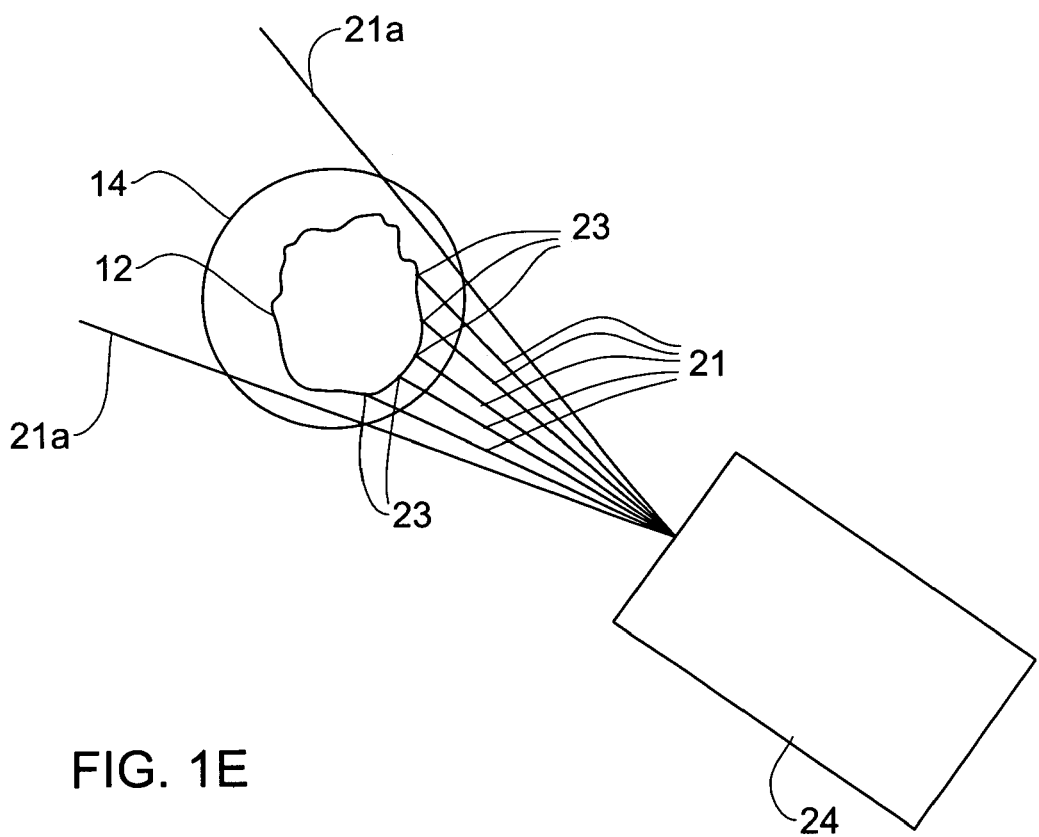
FIG. 1E is the closeup of FIG. 1D, with a gemstone supported by the platform.

The gemstone 12 illustrated in FIG. 1E is impinged upon by laser beams 21 at points 23, and not impinged upon by laser beams 21a. It will be appreciated that other gemstones may be provided which, in addition to not being impinged upon by extreme laser beams 21a, are not impinged upon by some of laser beams 21.

The laser beams may have any appropriate shape, e.g. they may be so shaped that the shape of their intersection with the plane P is in the form of a straight or curved line or a point.

One example of the laser illumination system that may be used in the described apparatus is 733L SNF laser supplied by StockerYale of Salem, Mass., USA. The pitch p between adjacent laser beams is 0.38°, and 33 laser beams are projected. The wavelength of the laser beams may vary between 635 nm and 830 nm.

The processor 26 is adapted to control the operation of the apparatus, to calculate a composite of the silhouettes of the gemstone to provide a convex envelope thereof, to calculate predicted reflections of each laser beam based on the calculated convex envelope, to compare captured reflections of the laser beams with predicted reflection thereof, as explained below, thereby determining the shape of the gemstone, including concavities.

In use, the gemstone 12 is placed upon the platform 14. The gemstone may be a cut stone, or a rough stone, and it may be coated with a removable diffuse substance as is known in the art, for example from U.S. Pat. No. 6,567,156, of which col. 3, line 47 through col. 4, line 2, is incorporated herein by reference. The platform 14 is rotated through two complete rotations.

During the first rotation, the backlight 16 illuminates the stone. The imaging system 22 scans the stone by capturing the image thereof at each one of a first set of predetermined angular positions. Each of these images is a silhouette of the stone. From the silhouettes, a three-dimensional representation of the gemstone 12 is calculated by the processor 26.

Figure 2B:
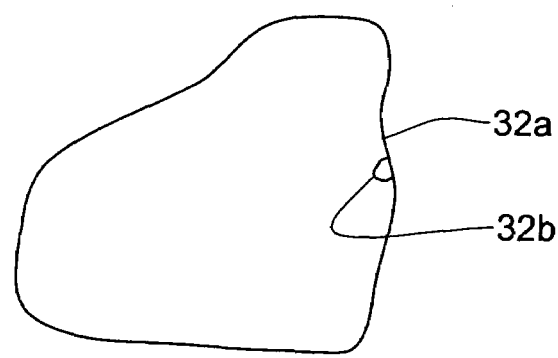
FIG. 2B is an outline of a silhouette of the gemstone illustrated in FIG. 2A, with the location of the defect indicated.

Since this representation is calculated using silhouette images, any concave feature (i.e., concavities) of the gemstone 12 will not be represented, as illustrated by FIGS. 2A and 2B.

It will be appreciated that since in order to calculate the convex envelope, the processor 26 must have awareness of the angular position of the gemstone 12 corresponding to each of the silhouettes, the rotation of the platform 14 may be controlled thereby.

Once the convex envelope has been calculated, the processor 26 carries out two processes—a prediction process and a refinement process. During the prediction process, the processor 26 predicts, based on the assumption that the actual geometry of the stone matches that of the convex envelope, where path of the captured reflection of each the laser beams will be detected by the imaging system. During the refinement process, the processor 26 compares the captured reflections of each of the laser beams with the results from the prediction stage to identify the locations and geometries of concavities on the surface of the gemstone. These two processes will be described below.

The prediction process takes advantage of the fact that the disposition of the illumination system 24 with respect to the imaging system 22 is known. Therefore, the processor predicts, for each one of the second set of angular positions of the gemstone, how a laser beam from the illumination system will be reflected therefrom, with the assumption that the actual shape of the gemstone corresponds to the shape of the convex envelope. Each predicted point (in the event that the illumination source 24 to be used projects a linear laser beam) or line (in the event that the illumination source projects a planar laser beam) is referred to as a predicted reflection. The prediction may be carried out by any known method, such as by triangulation. This prediction may be carried out at any time following the first rotation.

In order for the refinement process to proceed, the gemstone 12 undergoes a second rotation. During the second rotation, the illumination system 24 projects laser beams on the gemstone. The reflections of the laser beams are captured by the imaging system 22 at each one of a second set of predetermined angular positions of the gemstone during the second rotation. These positions may be the same positions at which silhouettes of the gemstone were captured during the first rotation.

It will be appreciated that while the second rotation and the projection of laser beams from the illumination system 24 on the gemstone 12 is a necessary step for the refinement process, they need not be carried out after the prediction process. The second rotation and the associated illumination may be carried out, and only then the prediction and refinement may be carried out. Alternatively, for each angular position of the gemstone, all three processes may be carried out simultaneously.

The captured reflections of each laser beam may be visually compared with its corresponding predicted reflection. It may be determined that there is no concavity in locations where the captured reflection substantially corresponds to the predicted reflection. If the captured reflection falls to the side of the predicted reflection, then there may be determined to be a concavity at that location. The extent of the concaveness is determined by the extent of the deviation by triangulation.

Figure 3:
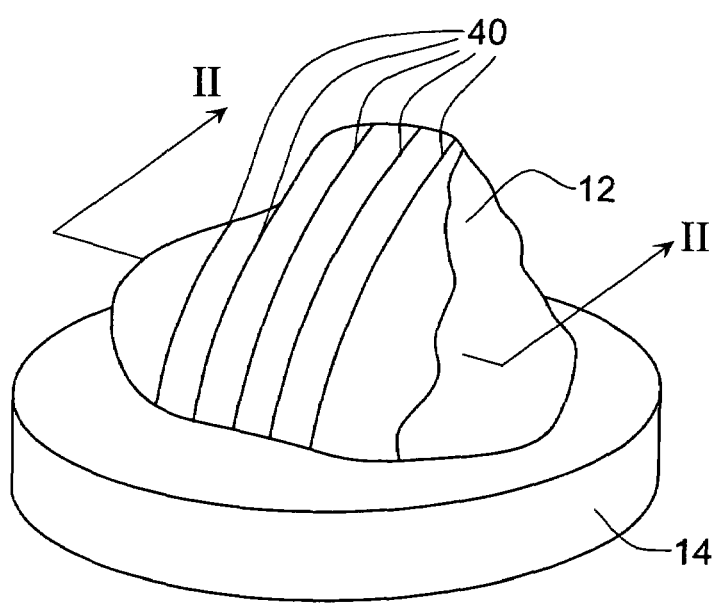
FIG. 3 illustrates the gemstone shown in FIG. 1, with a plurality of laser lo beams impinging thereon.
Figure 4A:
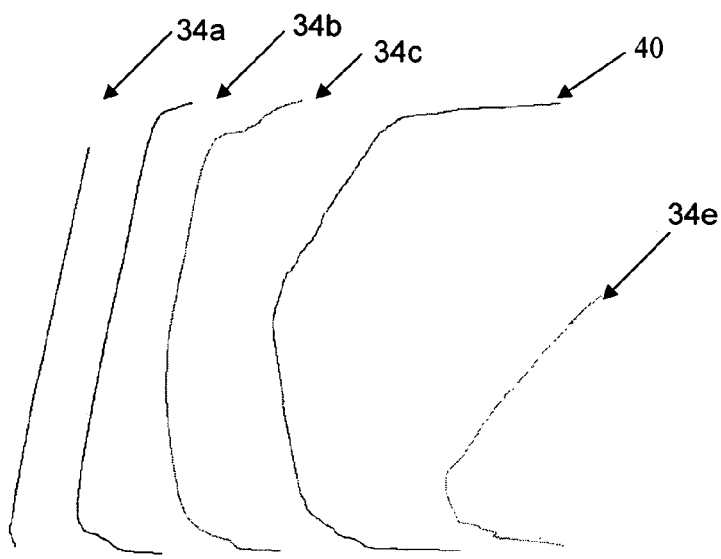
FIG. 4A illustrates predicted reflections of five laser beams from a laser illumination system, based on a convex envelope of the gemstone.
Figure 4B:
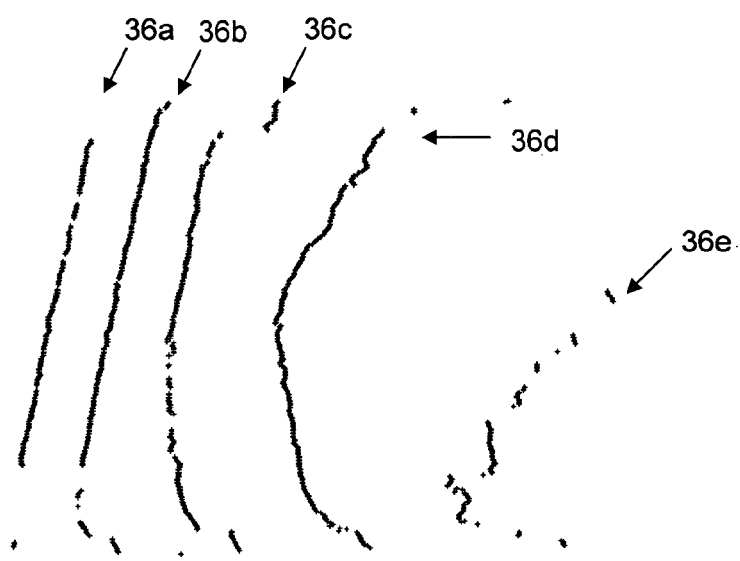
FIG. 4B illustrates captured reflections of the lasers beams from of the gemstone.
Figure 4C:
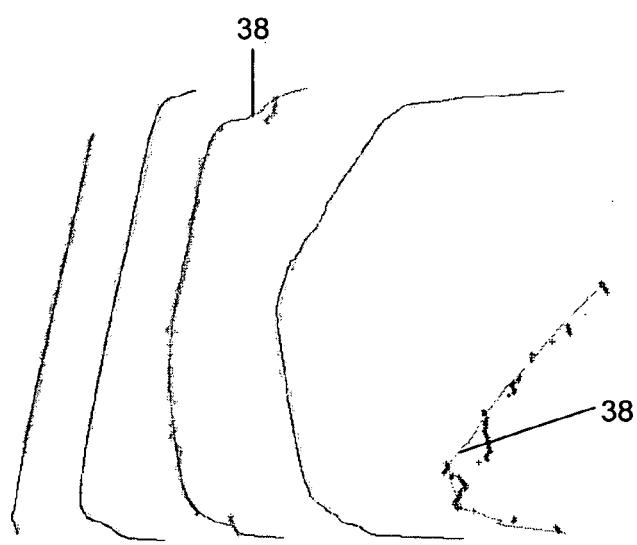
FIG. 4C illustrates the predicted reflections illustrated in FIG. 4A superimposed on the captured reflections illustrated in FIG. 4B.
Figure 5A:
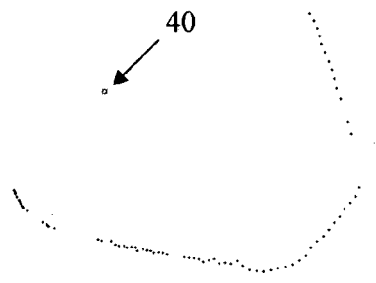
FIGS. 5A through 5G illustrate calculated points on the surface of the gemstone illustrated in FIGS. 3A through 3C, on a cross-section thereof.
Figure 5B:
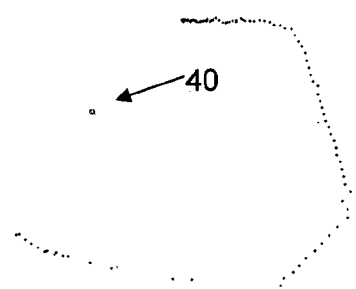
Figure 5C:
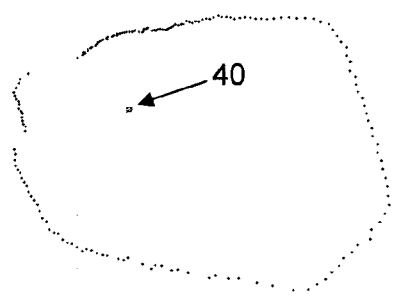
Figure 5D:
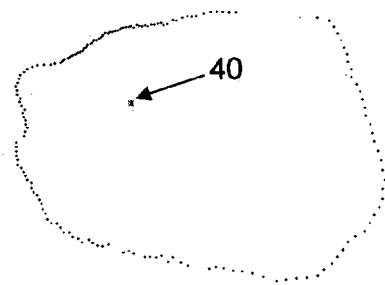
Figure 5E:
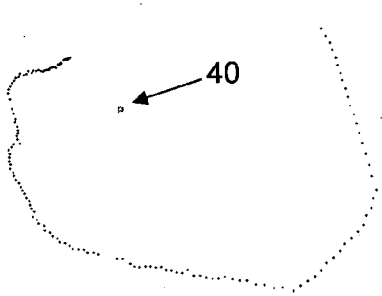
Figure 5F:
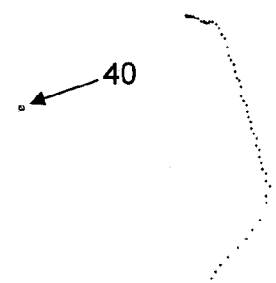
Figure 5G:
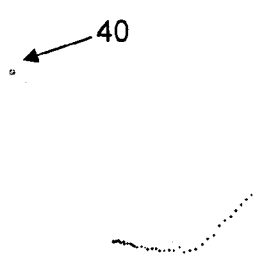

For example, laser beams are projected on the gemstone 12, as illustrated in FIG. 3. Lines 40 indicate where the laser beams impinge thereupon. FIG. 4A illustrates a series of predicted reflections 34a through 34e. Each of these lines corresponds to the predicted reflection of one of the laser beams from the illumination system 24 from a gemstone having a shape which corresponds to the shape of the convex envelope, wherein each laser beam is planar. It should be noted that the predicted reflections illustrated are calculated for a single angular position of the gemstone. FIG. 4B illustrates the captured reflections 36a through 36e, respectively, of each of the laser beams when the gemstone is at the same angular position used to calculate the predicted reflections. The captured reflections 36a through 36e are, in actuality, the point on the physical gemstone where the laser beam was reflected from. This is determined, e.g., using triangulation as known per se in the art. FIG. 4C illustrates the captured reflections 36a through 36e superimposed on their corresponding predicted reflections 34a through 34e.

During the refinement process, the processor 26 determines which captured reflection 36a through 36e corresponds to which predicted reflection 34a through 34e by noting where it falls in relation thereto; captured reflections from concavities will always fall to the same side of the predicted reflection. If the laser beam is projected from the right side of the gemstone, the captured reflection will fall to the left of its corresponding predicted reflection. Alternatively, the illumination system could be adapted to project laser beams having different wavelengths (i.e., colors) or may project each of the laser beams at a different time in order to differentiate among them.

Once the correspondence of the captured reflections 36a through 36e to their respective predicted reflections 34a through 34e has been determined, the locations of concavities can be seen by the deviations between the predicted reflections and the captured reflections, for example, in locations 38.

For each cross-section of the gemstone, such as the one indicated by line II-II in FIG. 3, the outline thereof is calculated. For each laser beam, for each angular position on the gemstone, the points of impingement on the cross-section are calculated, e.g., by triangulation. The points associated with a single laser beam and the cross-section for all of the angular positions are aggregated, as illustrated in FIGS. 5A through 5G for seven typical laser beams. The axis of rotation of the stone is indicated at 40 for reference.

It will be observed that not all of the sides of the gemstone have points associated with them for all of the angular positions. However, as seen in FIG. 6, when all of the images are superimposed, a complete picture of the outline of the gemstone at the cross-section emerges.

Figure 7:
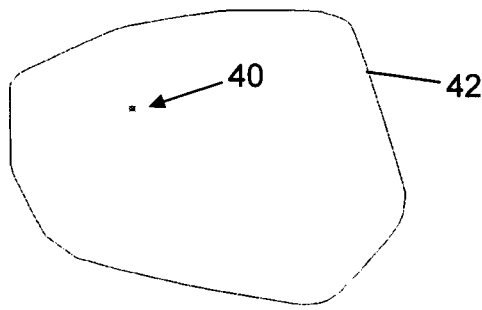
FIG. 7 illustrates a cross-section of the convex envelope of the gemstone.

In addition to the above, the cross-section of the convex envelope, generally indicated at 42 in FIG. 7, may be calculated. This calculation constitutes a portion of the prediction process, and may be performed at any time.

Figure 6:
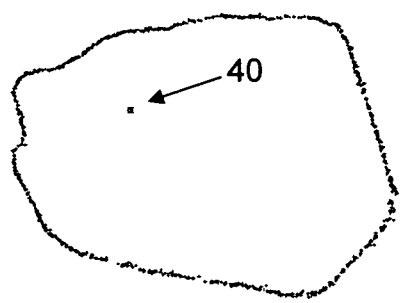
FIG. 6 illustrates the points of FIGS. 5A through 5G superimposed.
Figure 8A:
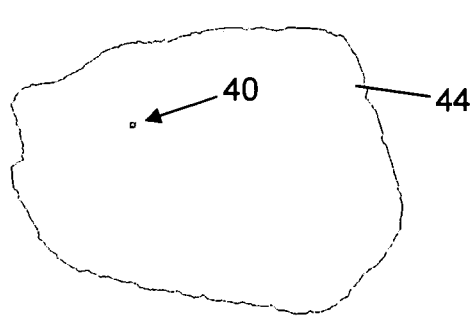
FIG. 8A illustrates the calculated outline of the gemstone.
Figure 8B:
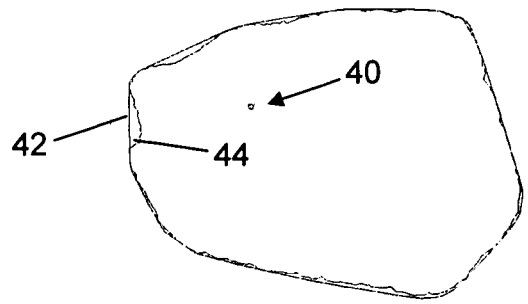
FIG. 8B illustrates the cross-section of FIG. 7 superimposed on the calculated outline illustrated in FIG. 8A.

A line, generally indicated at 44 and corresponding to the picture of the outline illustrated in FIG. 6, is calculated by the processor, as illustrated in FIG. 8A. For comparison, FIG. 8B illustrates the line 44 superimposed over the cross-section 42 of the convex envelope. In calculating the line 44, several considerations may be taken into account. Due to normal operational errors, such as noise, vibration, etc., several of the captured reflections may give inaccurate information regarding the location where its respective laser beam impinged upon the stone. Therefore, points which vary widely from points obtained by other laser beams in the same vicinity may be disregarded. Similarly, points which lay outside of the cross-section of the convex envelope may be disregarded.

As can be seen from the above, by providing several laser beams for imaging, more points on the surface of the gemstone are imaged multiple times, resulting in a more accurate calculation of the line 44. In addition, especially in deep concavities, a single laser beam will be insufficient to map the entire surface thereof, more explanations of which are provided below.

Figure 11E:
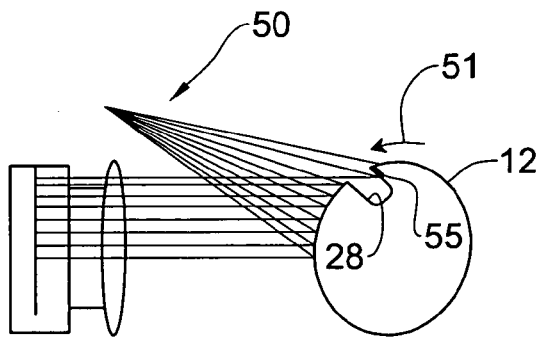
Figure 11F:
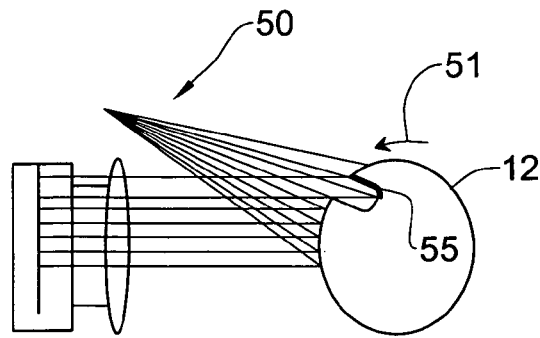
Figure 11G:
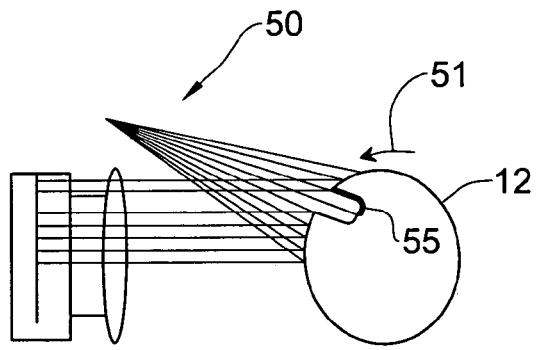
Figure 11H:
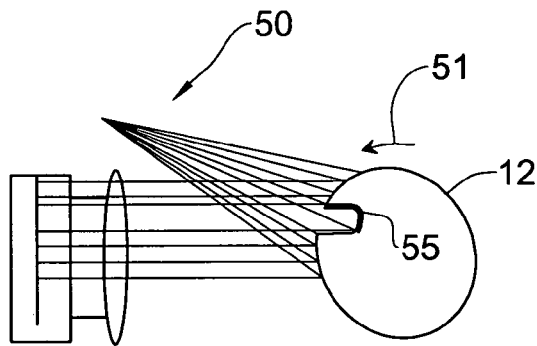
Figure 11J:
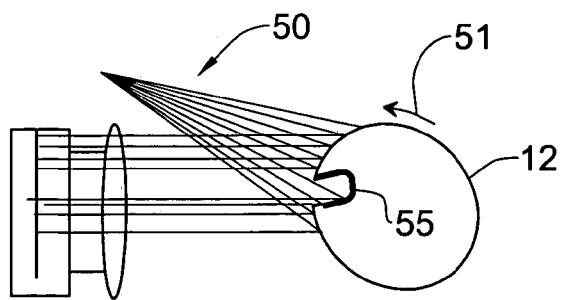

In FIGS. 11A and 11B, a gemstone 12 having a concavity 28 is impinged upon by a laser beam 50, which is reflected along path 50a. The gemstone rotates in the direction indicated by arrow 51. As the gemstone 12 rotates, the laser beam 50 impinges upon different parts of the surface of the gemstone 12. In the angular (i.e., rotational) range of the gemstone during which the laser beam 50 can both enter the concavity and be reflected therefrom in the direction of the imaging device 22 (the extreme positions of this range being illustrated in FIGS. 11A and 11B), only the region indicated at 55 is imaged by the single laser beam.

As illustrated in FIGS. 11C and 11D, the addition of a second laser beam 150, which is reflected along path 150a, directed from a different direction, only helps to a limited degree, since only the region indicated at 155 is imaged thereby.

Two factors contribute to the lack of imaging of the concavity when only a single laser beam is projected from each direction. A first is that the laser beam cannot reach all surfaces of the concavity. The second is that even among those points which are impinged upon by the laser beam, the line of sight between the point and the imaging system may be blocked by an opposing wall of the concavity.

As can be seen in FIGS. 11E through 11J, when a plurality of laser beams 50 are projected on the gemstone from the same direction at different angular positions, portions of the concavity 28, which is not impinged upon by a single laser beam, are imaged. In addition, the reflections of a greater number of the laser beams are detected by the imaging device 22. The result is that the region 55 which is imaged is greater than that which can be achieved with a single laser beam from each source alone.

In addition to the above, it will be appreciated that by providing several laser beams, more of the surface of the gemstone will be imaged more than once, providing greater accuracy and less noise, resulting in a more refined image.

Figure 9:
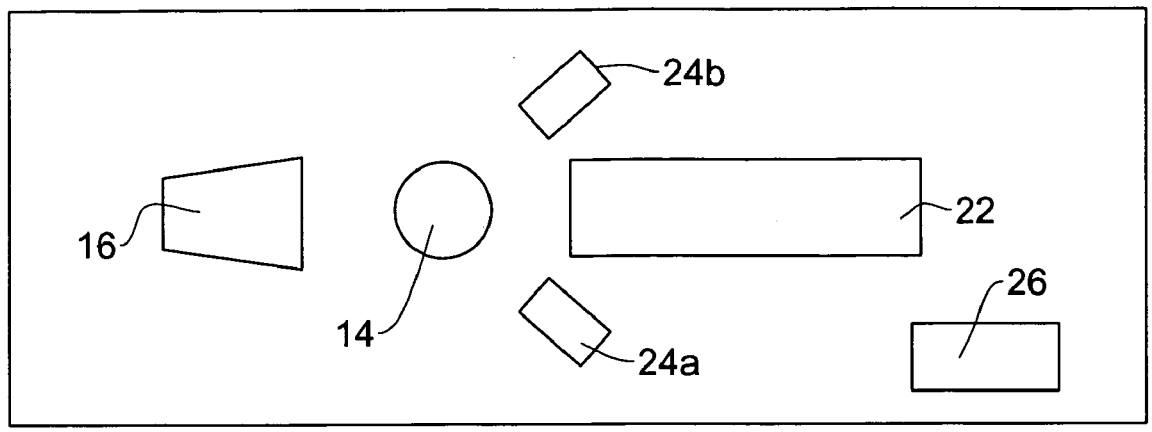
FIG. 9 is schematic illustration of another example of an apparatus according to the present invention.
Figure 10A:
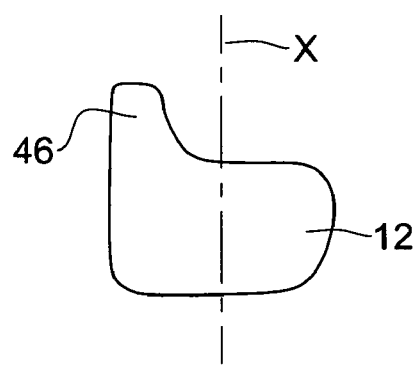
FIG. 10A is a side view of a gemstone.

Although the illumination system 24, as illustrated in FIG. 1, comprises a single laser source adapted to project several laser beams, the present invention is not limited to such an embodiment. As seen in FIG. 9, the illumination system may be split among two or more laser sources 24a and 24b. Each laser source may project one or more laser beams. In such a setup, at least one of the laser beams is spaced from the axis of rotation of the platform (i.e., it does not intersect it). This is useful, for instance, for use with a gemstone 12 such as the one illustrated in FIG. 10A, which comprises a portion 46 which projects upwardly therefrom, which is rotated about axis of rotation X.

Figure 10B:
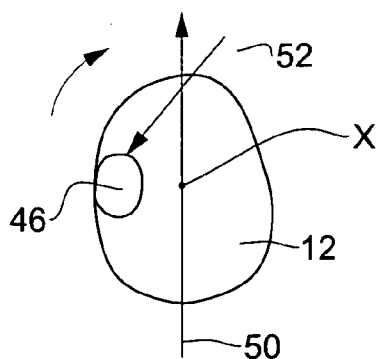
Figure 10C:
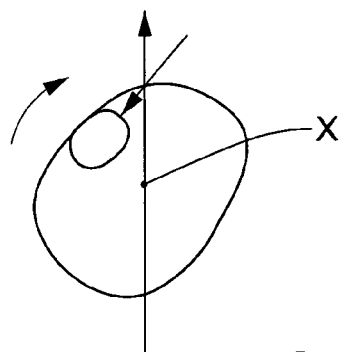
Figure 10D:
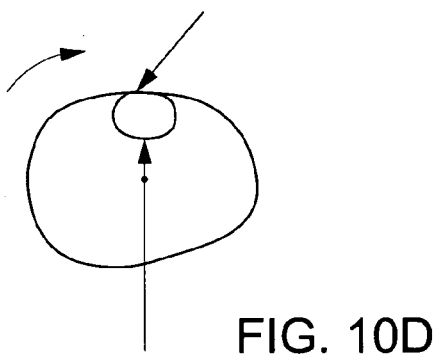
Figure 10E:
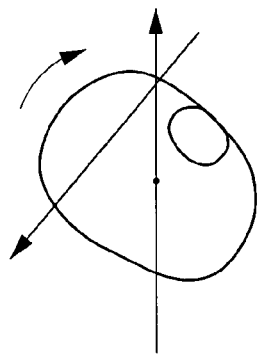
Figure 10F:
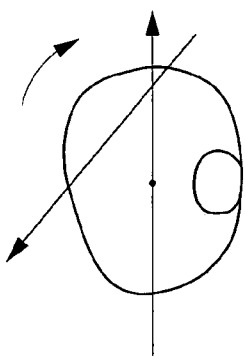
Figure 10G:
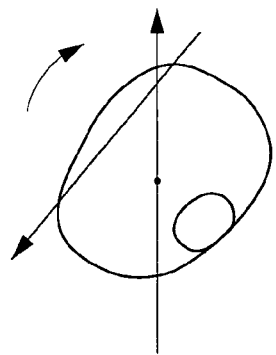
Figure 10H:
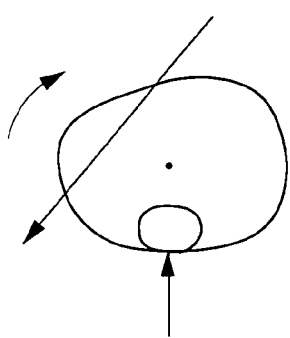
Figure 10J:
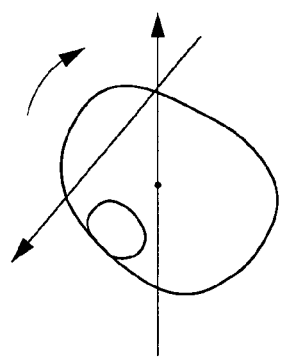

As illustrated in FIGS. 10B through 10J, as the gemstone 12 is rotated in a direction indicated by arrow 49, portion 46 is only impinged upon by a laser beam 50 passing through the axis of rotation X (hereinafter a "center-beam") during some parts of the rotation, and only some regions of the portion are impinged upon, as seen in FIGS. 10D and 10H. These same regions will be impinged upon irrespective of the direction from which the center-beam 50 projects. By projecting another laser beam 52 which does not pass through the axis of rotation X, other regions of portion 46 are impinged upon, as seen in FIGS. 10B, 10C, and 10D. In addition, parts of the regions impinged upon by the center-beam 50 are impinged upon more directly, which results in more accurate results.

When selecting a multi-beam laser source for use as the illumination system 24, several factors must be taken into account. The first is the resolution of the imaging system 22. Laser beams that are too close together may not be able to be distinguished by the imaging system. In addition, even if the imaging system can distinguish them, processing errors may result, such as the processor correlating a captured reflection with an incorrect predicted reflection, thereby performing calculations based on the correlation of a captured reflection with an incorrect laser beam. Laser beams which are too far apart, on the other hand, may miss certain features of the gemstone, i.e., the resolution of the composite three-dimension shape of the gemstone will be lower. In addition, an illumination system which provides laser beams which are too far apart may fail to project more than one laser beam which impinges upon a very small stone.

It will be understood that when discussing the distance between laser beams, reference is made to the distance when the laser beams impinge upon the gemstone. For laser beams which are parallel, this is the absolute distance therebetween. For diverging laser beams, the distance of the illumination system from the platform may be varied to obtain different distances.

Those skilled in the art to which this invention pertains will readily appreciate that numerous changes, variations and modifications can be made without departing from the scope of the invention mutatis mutandis. For example, the first rotation may be omitted if the convex envelope of the gemstone can be provided via other means.

The invention claimed is:

1. An apparatus for determining the shape of a gemstone including concavities on its surface, the gemstone having a size not smaller than a predetermined minimal size, the apparatus comprising:
   (a) a platform adapted to support the gemstone;
   (b) a scanning system adapted to provide geometrical information concerning the three-dimensional convex envelope of the gemstone;
   (c) an illumination system adapted to project on said gemstone illumination in the form of at least two laser beams along at least two separate optical paths;
   (d) an imaging system adapted to capture at least a portion of said illumination when reflected from the gemstone; and
   (e) a processor adapted to determine said shape based on the captured illumination and said geometrical information;
   the apparatus being adapted to rotate said gemstone with respect to the illumination system about an axis of rotation; at least one of said paths being spaced from said axis of rotation.

2. An apparatus according to claim 1, wherein the gemstone has a size not smaller than a predetermined minimal size, and said illumination system has an optical axis and is adapted to produce said laser beams such that they pass through a plane, which includes said axis of rotation and is oriented perpendicularly to said optical axis, at locations spaced apart from each other to a distance smaller than said minimal size.

3. An apparatus according to claim 1, wherein the gemstone has a size not greater than a predetermined maximal size, and said plurality of laser beams comprises a first extreme laser beam and a second extreme laser beam, all other laser beams being projected therebetween, wherein said extreme laser beams are spaced from each other at least in the vicinity of the platform to a distance greater than said maximal size of the gemstone.

4. An apparatus according to claim 1, wherein said processor is adapted to calculate, based on said geometrical information, a predicted reflection of each laser beam, to compare the captured reflections with said predicted reflections and to relate each captured reflection to its corresponding predicted reflection, to determine said shape of the gemstone based on the comparison and said geometrical information.

5. An apparatus according to claim 1, wherein the laser beams are linear so that the projection of each of them on the gemstone is in the form of a point.

6. An apparatus according to claim 1, wherein the laser beams are planar so that the projection of each of them on the gemstone is in the form of a line.

7. An apparatus according to claim 1, wherein the platform is adapted to rotate, thereby providing the rotation.

8. An apparatus according to claim 1, wherein the illumination system and the imaging system are adapted to rotate, thereby providing the rotation.

9. An apparatus according to claim 1, wherein the illumination system comprises a multi-beam laser source.

10. An apparatus according to claim 6, wherein each of said laser beams from the multi-beam laser source is disposed at an angle whose value is within the range of $0.05°$ and $10°$ with respect to adjacent laser beams.

11. An apparatus according to claim 1, wherein the illumination system comprises at least two laser sources, each of which projects at least one laser beam.

12. An apparatus according to claim 1, wherein the imaging system comprises a camera having a CCD.

13. An apparatus according to claim 1, wherein the scanning system comprises at least said imaging system and a light source facing said platform and being disposed substantially opposite the imaging system.

14. An apparatus according to claim 1, wherein the processor is adapted to calculate the convex envelope.

15. An apparatus according to claim 1, wherein said convex envelope is a composite of silhouettes of the gemstone provided by the scanning system.

16. An apparatus for determining the shape of a gemstone having a size being no greater than a predetermined maximal size, the apparatus comprising:
   (a) a platform adapted to support the gemstone;
   (b) a scanning system adapted to provide geometrical information concerning the three-dimensional convex envelope of the gemstone;
   (c) at least one laser source being adapted to project a plurality of laser beams, said plurality of laser beams comprising a first extreme laser beam and a second extreme laser beam, all other laser beams being projected therebetween;
   (d) an imaging system adapted to capture at least a portion of said illumination when reflected from the gemstone; and
   (e) a processor adapted to determine said shape based on the captured illumination and said geometrical information,
   wherein said extreme laser beams are spaced from each other at least in the vicinity of the platform to a distance greater than said maximal size of the gemstone.

17. An apparatus according to claim 16, wherein the gemstone has a size not smaller than a predetermined minimal size, and said illumination system has an optical axis and is adapted to produce said laser beams such that they pass through a plane, which includes said axis of rotation and is oriented perpendicularly to said optical axis, at locations spaced apart from each other to a distance smaller than said minimal size.

18. An apparatus according to claim 16, wherein said processor adapted to calculate, based on said geometrical information, a predicted reflection of each laser beam, to compare the captured reflections with said predicted reflections and to relate each captured reflection to its corresponding predicted reflection, to determine said shape of the gemstone based on the comparison and said geometrical information.

19. An apparatus according to claim 16, wherein the laser beams are linear so that the projection of each of them on the gemstone is in the form of a point.

20. An apparatus according to claim 16, wherein the laser beams are planar so that the projection of each of them on the gemstone is in the form of a line.

21. An apparatus according to claim 16, wherein each of said the laser beams from the laser source is disposed at an angle of 0.38° with respect to adjacent laser beams.

22. An apparatus according to claim 16, wherein the platform is adapted to rotate, thereby providing the rotation.

23. An apparatus according to claim 16, wherein the at least one laser source and the imaging system are adapted to rotate, thereby providing the rotation.

24. An apparatus according to claim 16, wherein the imaging system comprises a camera having a CCD.

25. An apparatus according to claim 16, wherein the scanning system comprises at least said imaging system and a light source facing said platform and being disposed substantially opposite the imaging system.

26. An apparatus according to claim 16, wherein the processor is adapted to calculate the convex envelope.

27. An apparatus according to claim 16, wherein said convex envelope is a composite of silhouettes of the gemstone provided by the scanning system.

28. An apparatus for determining the shape of a gemstone, the apparatus comprising:
   (a) a platform adapted to support the gemstone;
   (b) a scanning system adapted to provide geometrical information concerning the three-dimensional convex envelope of the gemstone;
   (c) an illumination system comprising at least one laser source, said illumination system being adapted to project on said gemstone illumination in the form of at least two laser beams along at least two separate paths;
   (d) an imaging system adapted to capture at least a portion of said illumination when reflected off the gemstone; and
   (e) a processor adapted to calculate, based on said geometrical information, a predicted reflection of each laser beam, to compare the captured reflections with said predicted reflections and to relate each captured reflection to its corresponding predicted reflection, to determine said shape of the gemstone based on the comparison and said geometrical information.

29. An apparatus according to claim 28, wherein the gemstone has a size not smaller than a predetermined minimal size, and said illumination system has an optical axis and is adapted to produce said laser beams such that they pass through a plane, which includes said axis of rotation and is oriented perpendicularly to said optical axis, at locations spaced apart from each other to a distance smaller than said minimal size.

30. An apparatus according to claim 28, wherein the relating is accomplished by determining the proximity of each of the captured reflections to a predicted reflection.

31. An apparatus according to claim 28, wherein the relating is accomplished by determining which side of each predicted reflection each captured reflection falls.

32. An apparatus according to claim 28, wherein each laser beam is of a different wavelength, the relating being accomplished by establishing the laser beam which corresponds to each of the captured reflections based on the wavelength thereof.

33. An apparatus according to claim 28, wherein each laser beam is projected at a different time, the relating being accomplished by establishing the laser beam which corresponds to the time at which each of the captured reflections is captured.

* * * * *